United States Patent [19]

Yahnke

[11] 4,060,566
[45] Nov. 29, 1977

[54] MEMBRANE PROCESS FOR SEPARATING MATERIALS

[75] Inventor: Robert L. Yahnke, Naperville, Ill.

[73] Assignee: Standard Oil Company (Indiana), Chicago, Ill.

[21] Appl. No.: 633,258

[22] Filed: Nov. 19, 1975

[51] Int. Cl.$^2$ .............................................. C07C 11/04
[52] U.S. Cl. ........................... 260/677 A; 260/683 D; 260/683.3
[58] Field of Search ...................... 260/677 A, 683.5 C

[56] References Cited

U.S. PATENT DOCUMENTS

| | | | |
|---|---|---|---|
| 3,770,842 | 11/1973 | Steigdman et al. | 260/677 A |
| 3,864,418 | 2/1975 | Hughes et al. | 260/677 A |

*Primary Examiner*—C. Davis
*Attorney, Agent, or Firm*—Bernard & Brown

[57] ABSTRACT

A process is disclosed for separating components, e.g., olefinically-unsaturated hydrocarbons, from mixtures with other materials by liquid barrier permeation and metal-complexing techniques using a semi-permeable membrane and a partial pressure differential across the membrane for the material being separated. The process is characterized by the use of elevated pressure on the feed side of the membrane, preferably at least about 200 psig, a low total pressure differential, if any, across the membrane, and preferably a partial pressure of the material being separated on the exit side of the membrane which is at least about 20 psi less than on the feed side. The separated material may be removed with advantage by the use of a liquid solvent in which the material is soluble, and preferably the concentration of the material in the solvent is up to about 25 weight percent of saturation when the solvent is charged to the exit side of the membrane. The separation of ethylene from its mixture with methane and ethane is of particular interest.

26 Claims, No Drawings

MEMBRANE PROCESS FOR SEPARATING MATERIALS

This invention relates to a process for separating a material from a fluid mixture containing the material by utilizing liquid barrier permeation and metal-complexing techniques wherein an aqueous liquid barrier containing metal-containing ions which form a complex with the material to be separated, is in contact with a semi-permeable membrane. The fluid mixture is supplied to one side of the membrane and separated material is removed from the other side of the membrane. In the method of the present invention, the rate of separation is increased by operating the input side of the membrane at an elevated total pressure of at least about 50 pounds per square inch gauge, and having a relatively low total pressure differential of the material separated between the feed and recovery sides of the semi-permeable membrane.

U.S. Pat. Nos. 3,758,603; 3,758,605; 3,770,842; 3,800,506; 3,844,735 and 3,864,418, to Steigelmann and Hughes are directed to methods for separating fluid materials such as aliphatically-unsaturated hydrocarbons and carbon monoxide from mixtures containing them, and involve the combined use of liquid barrier permeation and metal-complexing techniques which can exhibit high selectivity factors. In these processes, the liquid barrier is an aqueous solution having metal-containing ions which will complex with the fluid material to be separated, and the complexed material will, through a differential in partial pressure of the material between the feed and product sides of the semi-permeable membrane, be transferred across and released at the exit side of the semi-permeable membrane.

By the present invention, it has been found in processes of the foregoing described type that the rate of permeation of the material separated through the semi-permeable membrane is enhanced by operating at an elevated total pressure of at least about 50 pounds per square inch gauge on the feed side of the semi-permeable membrane and having a change in total pressure across the membrane which is up to about 25% of the total pressure on the feed side of the membrane. Stated in another way, the latter value for the total pressure on the product side is about 75 to 125% of the total pressure on the feed side of the membrane. In the process, a complex-forming, fluid material is separated from the feed mixture by contacting the latter with a first side of the membrane while having a partial pressure of the material on a second or product side of the semi-permeable membrane which is sufficiently less than the partial pressure of the material in the mixture to provide separated material on the second side of the membrane. The separated material can be removed from the vicinity of the second side of the membrane by, for instance, the use of a sweep, or purge, fluid which may be a gas or liquid.

In an aspect of the process of this invention, the total pressure on the feed side of the semi-permeable membrane is preferably at least about 100 psig or even at least about 200 psig. The total pressure on the product side of the semi-permeable membrane is elevated, and often is at least about 90 psig. Preferably, the total pressure on the product side is within about 10 psi of the total pressure on the feed side, or even within about 5 psi of the total pressure on the feed side, and within about 25% of the total pressure on the feed side. The total pressure on the product side of the semi-permeable membrane may exceed that on the feed side so long as there is a higher partial pressure of the material to be separated on the feed side compared with that on the product side of the semi-permeable membrane. Any difference in total pressure between the feed side and product side of the semi-permeable membrane should not, in any event, be so great as to rupture or otherwise by unduly deleterious to the semi-permeable membrane or separation effectiveness. When the total pressures on the feed and product sides of the membrane are substantially equal, high permeation rates with desirable product purities may be obtained. Conveniently, the total pressure of the feed is up to about 1000 psig; however, higher total pressures may be employed where desired.

The partial pressure of the material to be separated is greater on the feed side of the semi-permeable membrane used in this invention than the partial pressure of the material on the product side of the membrane. This partial pressure drop of the material to be separated is sufficient for the desired separation to result, and may often be at least about 0.5 pound per square inch, and is preferably at least about 20 pounds per square inch. The lower partial pressure of the material on the product side of the semi-permeable membrane may be maintained by employing a sweep, or purge, fluid to remove the material from the vicinity of the semi-permeable membrane. The sweep fluid is preferably inert to forming a complex or otherwise reacting with the metal-containing ions in the liquid barrier in contact with the semi-permeable membrane.

The sweep fluid which is used to remove the separated material from the vicinity of the product side of the semi-permeable membrane may be a liquid or a gas. The sweep fluid may be selected so that it can readily be separated from the components which have transferred across the membrane, if that be necessary or desireable for the subsequent use of the latter. Unless a reaction with the separated material is desired, the sweep fluid should be relatively inert therewith and may be, for instance, butane, carbon dioxide, or the like. The use as the sweep fluid of a liquid solvent in which the separated material is soluble may be beneficial since this may facilitate obtaining a desirable total pressure on the product side of the semi-permeable membrane, especially at high operating pressures. The sweep liquid, prior to contacting the exit side of the membrane, may contain dissolved separated material; however, it is preferred that the concentration of the material at this point be only up to about 25 percent of saturation. The sweep liquid may be essentially inert to forming a complex with the metal ions in solution in the liquid barrier, and may be substantially immiscible with the liquid barrier. The sweep liquid may have a sufficiently different boiling point than the product separated by the process, to be easily recovered by, for instance, flashing or distilling it from the desired product material, and a high purity product may thereby be obtained. The sweep liquid which is relatively free from the separated material may be returned to the separation process for removing further material from the product side of the semi-permeable membrane. The sweep liquid, however, may also serve in downstream processing of the separated material, either as a reactant, or as a solvent.

When employing a sweep liquid to remove the separated material from the vicinity of the product side of the semi-permeable membrane, the rate of solution of the separated material in the liquid may decrease with increased saturation of the liquid with the material. Generally, the sweep liquid after passing through the vicinity of product side of the semi-permeable membrane is less than saturated, for instance, up to about 70 weight percent saturated, preferably up to about 50 weight percent saturated. Typical sweep liquids which may be employed in the method of this invention, especially when the material separated is an aliphatically-unsaturated hydrocarbon, include liquid hydrocarbon solvents such as liquid paraffins, or mixtures containing paraffins, say normal or branched chain paraffins of four to ten or more carbon atoms, e.g., hexane, for instance, n-hexane, n-heptane, n-octane, n-nonane, and the like.

The temperature across the liquid barrier-semi-permeable membrane composite employed in the separation procedure of this invention can be essentially constant or it may vary, and decomposition of the metal complex can be effected primarily by the drop in partial pressure of the material to be separated on the product or exit side of the liquid barrier compared with its partial pressure on the feed side. Conveniently, the temperature of the liquid barrier may be essentially ambient, especially in the case of feedstocks that are gaseous at this temperature and the pressure employed on the feed side of the liquid barrier. The temperature of the liquid barrier may, however, be reduced or elevated from ambient temperature. Often, the temperature may be up to about 100° C., and elevated temperatures may even be desired to put the feedstock in the gaseous or vapor phase. Elevated temperatures, for instance, about 35° C. or more, may provide significant increases in permeation rates as compared to similar separation operations conducted at ambient temperatures. For instance, a 50% increase in permeation rate of ethylene may be noted by increasing the operating temperature from about 24° C. to 38° C. Neither the temperature nor the pressure used should, however, be such as to unduly reduce the difference in transport rate across the liquid barrier, semi-permeable film composite, of the material whose separation is sought, compared with that of the other components of the feed. The conditions should also not be such that physical disruption of the liquid barrier or any other significant malfunction results.

The process of the present invention may be employed to separate, for instance, one or more unsaturated hydrocarbons by the liquid barrier-complex-forming technique, and preferably by a procedure in which the barrier is at least partly contained in the membrane. Although the separated products provided may be quite pure materials, for instance, of greater than 99% purity, the separation procedure may be used merely to provide a significant increase in the concentration of a given material in a mixture with other components of the feedstock.

The process can be employed to separate various materials from other ingredients of the fluid feed mixture providing at least one of the materials exhibits a complexing rate or transfer rate across the liquid barrier that is greater than at least one other dissimilar or different component of the feedstock. Quite advantageously, the system can be used to separate aliphatically-unsaturated hydrocarbons from other hydrocarbons which may be aliphatically-saturated or aliphatically-unsaturated, or from non-hydrocarbon materials, including fixed gases such as hydrogen, having a lesser complexing rate or transfer rate across the liquid barrier than the material to be separated. The feed mixture may thus contain one or more paraffins, including cyclopar-affins, mono- or polyolefins, which may be cyclic or acyclic, and acetylenes or alkynes, and the mixture may include aromatics having such aliphatic configurations in a portion of their structure. Often, the feed mixture contains one or more other hydrocarbons having the same number of carbon atoms as the unsaturated hydrocarbon to be separated or only a one carbon atom difference. Among the materials which may be separated according to this invention are ethylene, propylene, butenes, butadiene, isoprene, acetylene and the like.

In the method, the mixture containing the material to be separated may be essentially in the gaseous or vapor phase when in contact with the liquid barrier having dissolved therein one or more metal-containing ions which form a complex with the material to be separated. The liquid barrier can be partially or essentially entirely within the semi-permeable membrane. The semi-permeable membrane is essentially impermeable to liquid flow therethrough under the conditions of use, and preferably is essentially impermeable to gaseous flow therethrough. The membrane can be said to somewhat immobilize the liquid barrier adjacent to or within the membrane, and the membrane in the presence of the liquid barrier is selective to the passage of the component of the feedstock to be separated. Since there is little, if any, passage for the feedstock across the separation zone except by becoming part of or reacting with the liquid barrier, this liquid barrier controls the selectivity of the liquid barrier-semi-permeable membrane combination.

The liquid barrier contains sufficient water and water-soluble, metal-containing ions to form a suitable complex with at least one component of the feed subjected to the separation procedure. The metal ions form the complex upon contact with the feed, and, in addition, the complex dissociates back to the metal-containing ion and a component of the complex which was in the feed, under the conditions which exist on the discharge side of the liquid barrier and semi-permeable membrane as employed in the process. The released feed component exits the discharge side of the membrane and can be removed from the vicinity of the barrier and its supporting structure as by a sweep fluid. Thus, the metal complex forms and is decomposed in the complex metal ion-containing liquid barrier, and, as a result, the material passing through the barrier is more concentrated with respect to at least one component present in the feed stream.

Often, the reactivity of aliphatically-unsaturated hydrocarbons with the complexing metal ions in their order of decreasing activity goes from acetylenes or dienes to mono-olefins, the aliphatically-saturated hydrocarbons and other materials present being essentially non-reactive. Also, different reactivities may be exhibited among the various members of a given type of aliphatically-unsaturated hydrocarbon. The process can thus be used to separate paraffins from monoolefins, diolefins or acetylenes; diolefins from monoolefins; or acetylenes from paraffins, monoolefins or diolefins; as well as to separate a given aliphatically-unsaturated hydrocarbon from another of such materials in its class where the members have differing complexing rates with, or transport rates across, the liquid barrier. The feed need only contain a small amount of aliphatically-unsaturated hydrocarbon, as long as the amount is sufficient so that the unsaturated material to be separated selectively reacts with the metal-containing ions to a significant extent, and thus at least one other component of the feed is less reactive or non-reactive with the complex-forming metal ions.

The aliphatically-unsaturated materials of most interest with regard to separation have 2 to about 8 carbon atoms, preferably 2 to 4 carbon atoms. The separation of aliphatically-unsaturated materials from admixtures containing other gaseous materials, such as the separation of ethylene or propylene from admixtures with other normally gaseous materials, e.g. one or more of ethane, propane, methane and hydrogen, is of particular importance. Frequently, such feed mixtures for the process contain about 1 to 50 weight percent ethylene, about 0 to 50 weight percent ethane and about 0 to 50 weight percent methane. Another process that may be of special significance is the separation from ethylene of minor amounts of acetylene.

The essentially solid, water-insoluble, semi-permeable membranes or films employed in the process of the present invention may be hydrophobic, but preferably are hydrophilic. Hydrophilic membranes permit the liquid barrier to be within the membrane at least to a significant extent. The hydrophilic membranes include membranes which contain additional hydrophilic and/or hygroscopic agents, and those that do not. A film membrane may be considered hydrophilic if it absorbs at least about 5 weight percent of water when immersed in distilled water for one day at room temperature and pressure. Typical membranes are those formed of film-forming materials such as nylon, e.g. the N-alkoxyalkyl polyamides, and those formed of nylon and more hydrophilic polymers such as polyvinyl alcohol, polyvinyl ethers, polyacrylamides and the like. The polymer materials may be formed into single membrane structures of desired configuration, as for example, by casting, or they may be formed into hollow fiber films by hot melt extrusion and subsequently bundled into an array. The hollow fiber membranes are preferred because they provide a large surface contact area for a given equipment volume. For instance, separation may preferably be achieved using hollow fiber membranes when the feed gas is passed to the outside of the fibers, the sweep fluid is passed through the inside of the fibers and the material undergoing separation passes from the outside to the inside of the hollow fibers. The advantages of our present process have been particularly good when operating in the latter way. In the operation of the method of the invention, the feed size of the fibers may preferably be flooded with the liquid barrier solution to enhance the separation of the desired material over a period of operation and prevent drying or selectivity loss of the membrane.

In the separation process the aqueous liquid barrier contains a metal component which provides in solution ions capable of forming a complex with the material desired to be separated from a fluid mixture. The source of the ions may be added to the membrane or be mixed with the polymer or film-forming constituents prior to formation of the film. The complex-forming component may be impregnated into the membrane in an aqueous or other form, and in any event, the membrane is in contact with sufficient water to form the aqueous liquid barrier when used in the separation process. The membrane may tend to dry during use even when the membrane contains major amounts of hydrophilic polymers. This drying may result in a considerable decrease in permeability and in selectivity for the separation and may be counteracted by, for instance, adding water or an aqueous solution containing the complex-forming metal to the feed side of the semi-permeable membrane, or by contacting the product side of the membrane with an aqueous liquid medium as described in co-pending application Ser. No. 498,112, filed Aug. 16, 1974, herein incorporated by reference.

The amount of water in the liquid barrier employed may be a minor portion of the liquid phase, but preferably is a major portion or even substantially all of the liquid, on a metal compound-free basis. Thus, small or minor amounts of water, say as little as about 5 weight percent, on a metal compound-free basis, in the liquid phase may serve to provide a significant transport across the liquid barrier of the material to be separated. Any other liquid present in the barrier is preferably water-miscible and should be chosen as not to have a substantial deleterious effect on the separation to be accomplished. The liquid barrier may also contain other materials in, e.g. minor amounts, such as hygroscopic agents to improve the wetting or hydrophilic properties of the liquid and provide better contact with the feed gas. The liquid barrier may contain minor but effective amounts of hydrogen peroxide to retard reduction of the complex-forming metal ions, e.g. silver, to their elemental forms.

The materials which can be employed to make the semi-permeable film membranes of the present invention may desirably be of the hydrophilic types that have been heretofore employed for the separation or purification of various chemical materials. Among these hydrophilic film-forming materials are those disclosed in U.S. Pat. Nos. 3,228,877 and 3,566,580, incorporated herein by reference. Most advantageously, however, the materials employed may have a film-forming nylon, e.g., an N-alkoxyalkyl polyamide, as an essential component. The polyamide film-forming materials are generally known and have also been designated as nylons or polycarbonamides. The polymers are characterized by having a plurality of amide groups serving as recurring linkages between carbon chains in the product structure, and the polymers may be made by several procedures.

The polyamide polymers which can be employed with particular advantage in this invention include those in which the film-forming polyamide is an N-alkoxyalkyl-substituted polyamide. Materials of this type are well known, as shown, for instance, by U.S. Pat. Nos. 2,430,910 and 2,430,923, which disclose N-alkoxymethyl polyamides made by the reaction of a polyamide polymer, formaldehyde and alcohol. Generally, at least about 5% of the amide groups of the polymer are substituted with alkoxyalkyl groups and such substitution may be up to about 60% or more. Preferably, this substitution is about 10 to 50% with the product being soluble in hot ethanol. The alcohols employed in making the N-alkoxyalkyl polyamides are generally monohydric and may have, for instance, from 1 to about 18 or more carbon atoms. The lower alkanols are preferred reactants, especially the lower alkanols having 1 to 4 carbon atoms. Among the useful alcohols are methanol, propanols, butanols, oleyl alcohol, benzyl alcohol, lauryl alcohol and alcohol ethers, for instance, the alkyl ethers of ethylene glycol.

The N-alkoxyalkyl polyamides which can be employed in the present invention to provide a desired semi-permeable membrane are preferably cross-linked and may be reacted with cross-linking agents or self-cross-linked as by acid catalysis at elevated temperatures. The cross-linking agents may be, for example, polycarboxylic acids, especially the dicarboxylic and tricarboxylic acids which may have, for instance, from 2 to 12 carbon atoms. Useful acids include oxalic acid, citric acid, maleic acid, and the like.

Film-forming membranes which can advantageously be employed in the present invention can be made by intimately combining, by either physical means or through chemical reaction, the N-alkoxyalkyl polyamide and a hygroscopic polymer material, e.g., the water-soluble polyvinyl alcohols. The polyamides and hygroscopic polymer may be used as a physical admixture or in various reacted forms, for instance, as cross-linked polymers or block or graft copolymers. The hygroscopic polymer is generally employed in an amount sufficient to enhance the hydrophilic properties of the polyamide and may be up to about 75 weight % or somewhat more of the membrane composition based on the total polyamide and hygroscopic polymer, and the latter is often at least about 5 or 15% and the amount is sufficient to impart a significant property to the film-forming combination. Preferably, each of the hygroscopic polymer and the polyamide are about 25 to 75% of their combination or total amount, or the hygroscopic polymer may be about 35 to 55% and the polyamide about 45 to 65% of their combination.

The film membranes of this invention may advantageously be made from a mixture-containing nylon, polyvinyl alcohol, di(lower alkyl) sulfoxide, and water as more fully described in copending U.S. Patent application Ser. No. 419,091 filed on Nov. 26, 1973, and incorporated herein by reference. The film membranes which can be employed in this invention are preferably in the form of thin hollow fibers and the feed may be passed to the outer side or inner side of the hollow fiber membrane.

A suitable process for making the fibers by extrusion involves providing the mixture having an elevated temperature suitable for extrusion, for instance, a temperature of about 60° to 125° C., preferably about 70° to 110° C. The material is extruded to form fibers having a hollow core surrounded by the membrane wall. During extrusion it is advantageous to pass a gas through the core of the hollow fibers to help cool the fibers and prevent the core of the fibers from closing. After extrusion the fibers can be dried to remove solvents and other low boiling materials. The resulting membranes have sufficient thickness so as not to be readily ruptured or otherwise undergo physical deterioration at a rate that would make their use unattractive. Generally the thickness of the fiber wall may be up to about 30 mils or more, preferably about 0.5 to 15 mils, and often the thickness is at least about 0.1 mil. The overall diameter of the fiber may usually be up to about 75 mils, preferably about 1 to 30 mils.

The properties, for instance, the strength and permeability, of the membrane fibers may be improved by drawing or stretching them and this can be accomplished at ambient or elevated temperatures. Suitable elevated temperatures include about 90° to 300° C., preferably about 125° to 200° C. The fibers may also be annealed at such temperatures, and the stretching and annealing may be accomplished simultaneously. The drawn fibers have a reduced overall diameter and thinner walls than before stretching whether at ambient or elevated temperature, and this treatment may preferably increase the length of the fibers by a factor of at least about 1.25, say up to about 10 or more. This treatment may decrease the thickness of the walls to where they are less than about 0.5 of the thickness they had before stretching. Excessive stretching may adversely affect the strength and performance of the fibers and thus we prefer that their length may not be increased by a factor of more than about 9. The stretching of the fibers is preferably accomplished when they are swollen with an aqueous or organic liquid. The swelling agent is preferably water. The amount of swelling agent present during stretching is often a minor amount up to about 50 weight percent of the fiber, preferably is at least about 1 weight percent.

In the present invention, the metal component in the liquid barrier solution, which metal may serve in the form of metal-containing cations to separate a component from a mixture through the formation of metal complexes of desired properties, include, for instance, the transition metals of the Periodic Chart of Elements having atomic numbers above 20. Among the useful metals are preferably silver and copper, especially the cuprous ions. Various combinations of the complex-forming metals may also be employed in this invention, either in the presence or absence of other non-metal or non-complexing metal components. The metal is provided in the aqueous liquid barrier of the separation system in a form which is soluble in this liquid. Thus, the various water-soluble salts of these metals can be used such as the nitrates and halides, for instance, the bromides and chlorides, fluoborates, fluosilicates, acetates, carbonyl halides or other salts of these metals which can serve to form the desired water-soluble complexes when the film is in contact with water. The metal salts should not react with any components of the chemical feedstock used in the separation procedure to form an insoluble material which could block the film membrane or otherwise prevent the separation of a component from the feedstock. Also, in a given system, the metal is selected so that the complex will readily form, and yet be sufficiently unstable, so that the complex will decompose and the dissociated material leave the liquid barrier, thereby providing a greater concentration of the material to be separated from the product side of the membrane than is in the feed. The concentration of the metal ions in the liquid barrier may be rather low and still be sufficient to provide an adequate complexing rate so that excessive amounts of the semi-permeable membrane surface will not be needed to perform the desired separation. Conveniently, the concentration of the complex-forming metal ions in the aqueous solution forming the liquid barrier is at least about 0.1 molar and is preferably about 0.5 to 12 molar. Advantageously, the solution is less than saturated with respect to the complex-forming metal ions to insure that essentially all of the metal stays in solution, thereby avoiding any tendency to destroy the permeability characteristics of the membrane.

When the complexing ions in the liqid barrier employed in this invention include cuprous ions, ammonium ions can be used to provide copper ammonium complex ions which are active to form a complex with the material to be separated by the use of the film. It is preferable to supply about equimolar amounts of cuprous and ammonium ions, although either type of ions may be in excess. The ammonium ions can be provided in various convenient ways, preferably as an acid salt such as ammonium chloride or as ammonium hydroxide or ammonium carbonate. In order to enhance the selectivity of the copper ammonium ion complex in the separation of this invention, the film and thus the liquid barrier solution may be made more acidic, by, for instance, providing a water-soluble acid such as a mineral acid, especially hydrochloric acid in the film or liquid barrier solution. Preferably, the pH of the liquid barrier in this form of the invention is below about 5 with the acid in the solution. Since silver may form undesirable acetylides with acetylenes, the copper ammonium complex may be a more attractive complexing agent when it is desired to use the film to separate acetylenes from various mixtures.

This invention will be further illustrated by the following specific examples.

EXAMPLE 1

Fiber membranes are employed to effect the separation of ethylene from a gaseous mixture of 31.7 mole percent methane, 35.8 mole percent ethylene, and 32.5 mole percent ethane. The fiber membranes are prepared from a polymer mixture containing about 60 weight percent of formaldehydealcohol modified 6:6 nylon (BCI-819, Belding Chemical Industries) and about 40 weight percent of water-soluble polyvinyl alcohol. The hollow fibers are formed by extrusion of the mixture through an annular die. The fibers are stretched at a temperature of 125° C. with an applied axial force of 300 grams and then annealed at 170° C. for 10 minutes. Ten fiber membranes are made, each with an exposed active length of 17 inches and an inside diameter of 0.006 inch and an outside diameter of 0.020 inch. The fibers are assembled into a vertical tube and shell permeator using an epoxy encapsulating agent (Armstrong C-4 with Activator D, available from Armstrong). The shell side of the permeator has an effective volume of about 5 milliliters.

A 4 molar aqueous solution of silver nitrate which contains 0.5 volume percent hydrogen peroxide and 10 volume percent glycerine is added on the shell side of the permeator at the rate of about 4 milliliters per minute, trickles down the fibers and exits at the bottom of the permeator. The gaseous feed is passed to the shell side of the membranes at a rate of about 26 milliliters per minute and nitrogen is employed as the sweep gas and flows through the membrane bores at a rate of about 10 milliliters per minute. The system is maintained at a temperature of about 24° to 24.5° C. The permeation rates of ethylene at various operating pressures on the feed and product sides of the membranes are provided in Table A.

TABLE A

| Pressures, psig | | | | Avg. ΔP Across Membrane, psi | Permeation Rate ml/min/cm² × 10³ | Ethylene in Permeate, Wt. % (Nitrogen free basis) |
| --- | --- | --- | --- | --- | --- | --- |
| Feed Side | Permeate Side | | | | | |
| | Inlet | Outlet | Avg. | | | |
| 300 | 7 | 3 | 5 | 295 | 12.0 | 98.97 |
| 300 | 92 | 88 | 90 | 210 | 13.3 | 98.95 |
| 300 | 152 | 148 | 150 | 150 | 14.7 | 98.96 |
| 300 | 250 | 246 | 248 | 52 | 16.8 | 98.98 |
| 300 | 299 | 295 | 297 | 3 | 17.5 | 98.94 |
| 100 | 98 | 94 | 96 | 4 | 11.1 | 99.46 |

It is considered that at a pressure of 300 psig on the feed side, the ethylene partial pressure driving force is 112 psi and at 100 psig, 41 psi.

The results indicate that a low total pressure differential between the feed and product side of the membrane provides an improved permeation rate of olefin as compared to a similar separation but in which a high total differential pressure exists between the feed and product sides of the membrane. Also, it is shown that the permeation rate of olefin is increased with increased operating pressure of the system.

Instead of employing nitrogen as the sweep gas, helium, butane or other gas may be employed. A liquid, such as n-hexane, may be employed as the sweeping fluid as is illustrated in the following example.

EXAMPLE 2

Fiber membranes of essentially the same composition as the fiber membranes used in Example 1 are employed in a similar manner to that described in Example 1 to effect the separation of ethylene from a gas containing approximately equal volumes of methane, ethylene, and ethane. Twenty of the fiber membranes, which have an inside diameter of 0.005 inch and an outside diameter of 0.013 inch and each having an exposed active length of 17 inches, are potted to provide a vertical shell and tube-type permeator. The complexing solution which is a 4 normal aqueous solution of silver nitrate containing 0.5 volume percent hydrogen peroxide and 10 volume percent glycerine, is fed to the shell side of the permeator to wet the fiber membranes. The permeator is operated as a flooded cell, and the feed gas is bubbled through the aqueous solution on the shell side of the permeator at a rate of about 15 milliliters per minute and a pressure of about 100 psig. Flowing in the same direction as the gas, liquid hexane is passed within the fiber membrane tubes at a rate of about 0.05 milliliters per minute and a pressure of about 75 psig to absorb the ethylene product with no gas phase present. The hexane-ethylene mixture leaving the permeator is partially flashed by passing it to a vessel at atmospheric pressure. The entire operation of permeation and flashing is conducted at room temperature. The gas and liquid streams from the flashing operation are analyzed individually for the feed components and are summed to determine the permeation rate and composition. The product analysis provides essentially the same purity of ethylene which can be achieved at the same conditions, including total pressure differential and ethylene partial pressure differential across the membrane, except employing a sweep gas such as nitrogen or helium. The permeation rate is also similar.

EXAMPLE 3

The procedure of Example 2 is essentially repeated employing a feed gas containing 34 mole percent methane, 35 mole percent ethylene, and 31 mole percent ethane, at feed gas pressure of 300 psig and hexane purge outlet at a pressure of 295 psig. The hexane purge withdrawn from the permeator is about 20 percent of complete saturation with ethylene at the operating conditions and the product gas contains 99.0 mole percent ethylene, and 0.5 mole percent of each of methane and ethylene. The lean tail gas from the permeator comprises 51 mole percent methane, 2 mole percent ethylene, and 47 mole percent ethane. The differential in partial pressure of ethylene in the feed and in the hexane purge is determined at the feed inlet end (hexane purge exit) to be 49 psi, and at the lean tail gas exit end (hexane purge inlet) to be 6 psi. The partial pressure of a material dissolved in or mixed with a liquid solvent is considered herein to be the value determined by multiplying the vapor pressure of the dissolved material by the mole percent of the dissolved material in the composition, divided by 100.

The procedure of this Example 3 is employed at different levels of ethylene content in the exiting hexane purge, and the differential in partial pressures of ethylene in the feed and in the hexane purge at the feed inlet end and the tail gas exit end are determined. At a hexane purge saturation of 5 percent, the feed inlet end differential is 95 psi and the tail gas exit end differential is 6 psi; and at a hexane purge saturation of 33 percent, the feed inlet end differential is 9 psi and the tail gas exit end is 6 psi.

EXAMPLE 4

In this example, gaseous nitrogen and liquid hexane are used alternately as the sweep medium flowing through the bore of a fiber membrane to obtain a direct comparison of their effectiveness. A single fiber membrane of essentially the same composition as the fiber membranes used in Example 1 is prepared. After extrusion, the fiber is stretched at 130° C. to 225 percent of its original length and annealed at 170° C. for 10 minutes. The fiber having an active length of about 38 feet with an inside diameter of 0.0076 inch and an outside diameter of 0.020 inch is wound on a 1/16-inch diameter mandrel to form a helical coil. The coil is assembled into a vertical shell and tube type permeator. The shell side, about 38 inches long, has an effective volume of about 11 milliliters.

A 4-molar aqueous solution of silver nitrate which contains 0.5 volume percent hydrogen peroxide and 10 volume percent glycerine is added to the shell side of the permeator at the rate of 4 milliliters per minute to trickle down the fiber and exit at the bottom. The permeator is employed in a similar manner to that described in Example 1 to effect the separation of ethylene from a gaseous feed containing 33.2 mole percent methane, 36.2 mole percent ethylene, and 30.6 mole percent ethane. The gaseous feed is passed to the shell side of the membrane at a rate of about 11 milliliters per minute to flow concurrent with the aqueous solution. The system is maintained at a temperature of about 24° to 24.5° C. Gaseous nitrogen, when used as the sweep medium, flows through the membrane bore countercurrent to the feed at a rate of about 7 milliliters per minute. The permeation rate of ethylene is 0.0079 milliliters per minute per square centimeter of membrane area and the purity of the permeate is 98.0 weight percent ethylene. Alternately, liquid hexane, when used as the sweep medium, flows in the same manner through the fiber bore at a rate of about 0.35 milliliters per minute to absorb essentially all of the permeated gases. The permeation rate of ethylene is 0.0070 milliliters per minute per square centimeter and the purity of the permeate is 98.2 weight percent ethylene.

It is claimed:

1. A process for separating a material from a fluid mixture comprising contacting said mixture containing said material with a first side of an essentially solid, water-insoluble, semi-permeable membrane having in contact therewith an aqueous liquid barrier having metal-containing ion which combine with said material to form a water-soluble complex, the partial pressure of said material on a second side of the semi-permeable membrane being sufficiently less than the partial pressure of said material on said first side to provide separated material on the second side of the semi-permeable membrane, and removing said separated material from the vicinity of the second side of the semi-permeable membrane, wherein the total pressure on the second side is about 75 to 125% of the total pressure of the mixture on the first side, and the latter total pressure is at least about 50 psig.

2. The process of claim 1 wherein the semi-permeable membrane is in hollow fiber form.

3. The process of claim 2 in which said first membrane side is the outer side of the hollow fiber membrane.

4. The process of claim 2 in which the fluid mixture contains ethylene, methane and ethane, and ethylene is separated.

5. The process of claim 4 in which said metal-containing ions are silver ions.

6. The process of claim 1 in which said removal from said second side involves contacting said second side with a liquid solvent in which said separated material is soluble.

7. The process of claim 6 in which the liquid solvent used to remove the separated material is up to about 25% saturated with the latter when initially contacted with said second side.

8. The process of claim 7 in which said separated material is olefin of 2 to 4 carbon atoms.

9. The process of claim 8 in which said olefin is comprised of ethylene and said mixture contains ethylene, methane and ethane.

10. The process of claim 9 in which said metalcontaining ions are silver ions.

11. The process of claim 10 in which said solvent is comprised of paraffin.

12. The process of claim 10 in which said membrane is in hollow fiber form and said first side is the outer side of said fiber.

13. A process for the separation of a material from a fluid mixture comprising contacting said mixture containing said material at a total pressure of at least about 200 psig with a first side of an essentially solid, water-insoluble, hydrophilic, semi-permeable membrane having at least partially therein an aqueous liquid barrier having dissolved therein metal-containing ions which combine with said material to form a water-soluble complex, the partial pressure of said material on a second side of the semi-permeable membrane being sufficiently less than the partial pressure of said material on said first side to provide separated material on the second side of the semi-permeable membrane, said partial pressure on said first side being at least about 20 psi greater than said partial pressure on said second side, and removing said separated material from the vicinity of the second side of the semi-permeable membrane, wherein the total pressure on the second side of the semi-permeable membrane is within about 10 psi of that of said first side.

14. The process of claim 13 wherein the semi-permeable membrane is in hollow fiber form.

15. The process of claim 14 in which said first membrane side is the outer side of the hollow fiber membrane.

16. The process of claim 14 in which the fluid mixture contains ethylene, methane and ethane, and ethylene is separated.

17. The process of claim 16 in which said metal-containing ions are silver ions.

18. The process of claim 13 in which said removal from said second side involves contacting said second side with a liquid solvent in which said separated material is soluble.

19. The process of claim 18 in which said separated material is olefin of 2 to 4 carbon atoms.

20. The process of claim 19 in which said olefin is comprised of ethylene and said mixture contains ethylene, methane and ethane.

21. The process of claim 20 in which said metal-containing ions are silver ions.

22. The process of claim 21 in which said solvent is comprised of paraffin.

23. The process of claim 21 in which said membrane is in hollow fiber form and said first side is the outer side of said fiber.

24. The process of claim 1 in which said membrane comprises nylon.

25. The process of claim 14 in which said membrane comprises nylon.

26. The process of claim 25 in which said membrane comprises N-alkoxyalkyl polyamide.

* * * * *

UNITED STATES PATENT OFFICE
CERTIFICATE OF CORRECTION

Patent No. 4,060,566      Dated November 29, 1977

Inventor(s) Robert L. Yahnke

It is certified that error appears in the above-identified patent and that said Letters Patent are hereby corrected as shown below:

Column 8, line 56, "liqid" should be --liquid--.

Column 9, line 31, after "C-4" the word --Resin-- was omitted.

Column 9, line 43, "10" should be --100--.

Column 9, line 66, "side" should be --sides--.

Column 11, line 41, "concurrent" should be --cocurrent--.

Column 11, line 62, claim 1, "ion" should be --ions--.

Column 12, line 30, claim 10, "metalcontaining" should be --metal-containing--.

Signed and Sealed this

Twenty-eighth Day of March 1978

[SEAL]

Attest:

RUTH C. MASON
*Attesting Officer*

LUTRELLE F. PARKER
*Acting Commissioner of Patents and Trademarks*